United States Patent [19]
Sato et al.

[11] Patent Number: 5,869,768
[45] Date of Patent: Feb. 9, 1999

[54] MATERIAL TESTING DEVICE, MATERIAL TESTING APPARATUS AND MATERIAL TESTING METHOD

[75] Inventors: Kazuo Sato, 2-1605, Kifune; Mitsuhiro Shikida, 107, Atorasu, 2-231, Fujimori, both of Meito-ku, Nagoya-shi, Aichi, Japan

[73] Assignees: Seiko Instruments Inc.; Kazuo Sato; Mitsuhiro Shikida, all of, Japan

[21] Appl. No.: 797,548

[22] Filed: Feb. 7, 1997

[30] Foreign Application Priority Data

Feb. 8, 1996 [JP] Japan ................................. 8-022860

[51] Int. Cl.$^6$ ................................................. G01N 19/06
[52] U.S. Cl. ............................................................ 73/783
[58] Field of Search ............................... 73/790, 812, 813, 73/818, 777, 821, 824, 826, 843, 849, 862.636, 862.634, 862.628, 783–793

[56] References Cited

U.S. PATENT DOCUMENTS

| | | | |
|---|---|---|---|
| 3,410,133 | 11/1968 | Savage | 73/851 |
| 3,868,849 | 3/1975 | Hunyar | 73/854 |
| 4,522,072 | 6/1985 | Sukouff et al. | 73/862.628 |
| 4,823,607 | 4/1989 | Howe et al. | 73/783 |
| 5,209,119 | 5/1993 | Polla et al. | 73/862.636 |
| 5,526,697 | 6/1996 | Tada et al. | 73/862.634 |

*Primary Examiner*—Ronald L. Biegel
*Attorney, Agent, or Firm*—Adams & Wilks

[57] ABSTRACT

A material testing device 1 is constituted by a test piece 2, the mechanical properties of which are to be measured and which is connected to the test piece 2, a pair of torsion bars 4 operating as an elastic support portion of the rotary lever 3 and a frame 5 functioning as a rigid support portion of the test piece 2 and the torsion bars 4 and forming an outside frame, the mechanical properties of the test piece 2 are measured by applying an uniaxial tensile force on the test piece 2 in a direction of arrow marks A—A by applying a vertical load W on one end of the rotary lever 3. The test piece 2 is integrally formed with the frame 5 and the rotary lever 3 and therefore, the mechanical property values can easily be measured with no direct contact to the test piece 2.

18 Claims, 7 Drawing Sheets

MATERIAL TESTING DEVICE, MATERIAL TESTING APPARATUS AND MATERIAL TESTING METHOD

BACKGROUND OF THE INVENTION

The present invention relates to a material testing device for testing mechanical properties of a very fine material in a thin film form by applying a stress on the material, a material testing apparatus for carrying out the test and a method of testing the material.

Intensive researches are carried out on the micromachining technology of a semiconductor, or the MEMS (Micro-Electro-Mechanical Systems) in which a mechanical structure having a size of several tens through one hundred μm is prepared by using, for example, photolithography, etching, thin film forming technology or the like and the mechanical structure is applied to a sensor, an optical element or a mechanical device, or on a micromachine. With respect to such a new device, a single crystal of silicon or an oxide film, a nitride film or the like formed on the surface of the single crystal of silicon is used in place of a conventional metal material such as steel or the like.

The mechanical properties such as elastic modulus, yield stress or the like of these materials are important factors controlling the function of the device of the MEMS. Meanwhile, it is known that the mechanical properties of these thin films are significantly varied by the manufacturing processes of these and therefore, and the importance of the method of measuring and evaluating these materials has been emphasized.

As conventionally proposed methods of measuring and evaluating these materials, there are methods where a diaphragm is prepared by a thin film and an amount of bulging of the diaphragm when an air pressure is applied thereon, is measured, a method using a micro hardness tester in which an indenter is pushed into a test piece, a method in which a very small tensile test piece is prepared and the test piece is pulled by attaching the test piece to a tensile tester or the like.

However, according to the conventional method of measuring the amount of bulging of a diaphragm, although the elastic modulus can be measured, the yield stress cannot be measured. Further, although the method of using a micro hardness tester for pushing in an indenter into a test piece, is simple for evaluating the yield stress of a ductile metal, the method is difficult to apply to a brittle material such as silicon and compounds of silicon.

Although the method using a tensile tester is one of the most preferable testing methods in evaluating the mechanical properties, when a very small test piece that is easy to destruct, is chucked or adhered to a tensile tester, the brittle test piece may be destructed, or a bending stress may be superposed thereon because the axis of the test piece is not in alignment with the axis of tension, or the like. Further, the measurement accuracy of strain may be low since the displacement in elongating the test piece having a short gage length is small.

SUMMARY OF THE INVENTION

It is an object of the present invention to realize a system of carrying out a tensile test with no direct contact to a very small test piece.

It is another object of the present invention to realize a system which has a high measurement accuracy of strain in a case that the displacement in elongating a test piece having a small gage length is small.

In order to realize the system according to the present invention, a test piece is integrally formed with a material testing device to carry out the tensile test with no direct contact therewith. According to the present invention, there is provided a material testing apparatus having a function of applying a uniaxial tensile force on a test piece by applying a vertical load on the material testing device. Further, according to the present invention, there is provided a method of testing a material by which the mechanical properties of a material constituting a test piece are measured and evaluated by applying a uniaxial tensile stress on the test piece by the material testing device with no direct contact to the test piece.

According to the present invention, the test piece per se is not brought into direct contact with a tester and therefore, the above-described various problems in attaching the test piece to a tensile tester are resolved and the measurement accuracy can be improved.

DETAILED DESCRIPTION OF THE PREFERRED EMBODIMENTS

Figure 1:
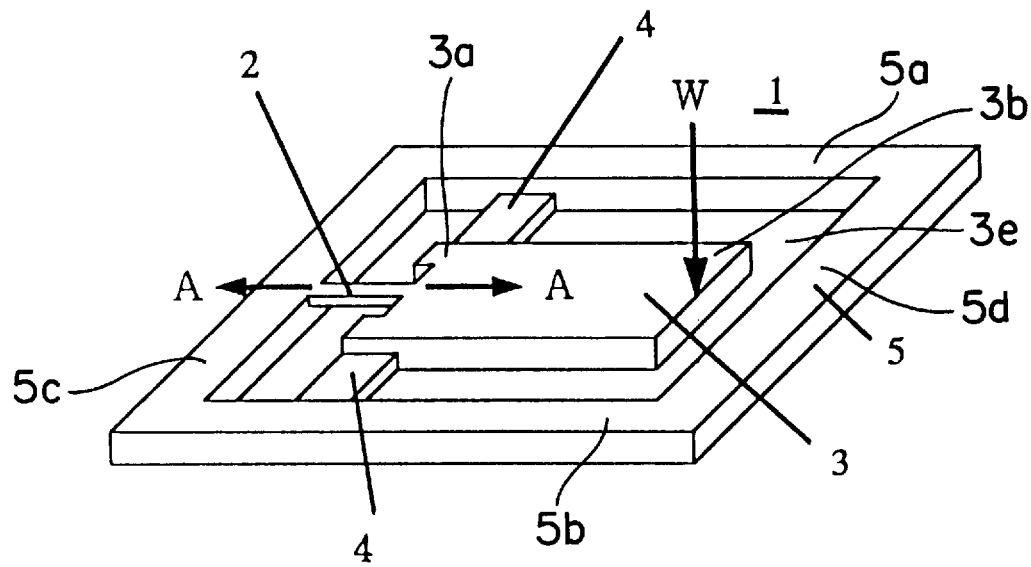
FIG. 1 is a perspective view showing an embodiment of a material testing device according to the present invention.

According to the present invention a material testing device is constituted by a test piece, a rotary lever for applying a predetermined stress on the test piece, an elastic support portion for supporting elastically the displacement of the rotary lever and a rigid supporting portion for supporting rigidly the test piece and the elastic supporting portion.

Further, the mechanical property values of a single crystal of silicon can be measured by constituting the test piece, the rotary lever, the elastic supporting portion and the rigid supporting portion integrally by the single crystal of silicon.

Further, the test piece maybe a thin film comprising a tested material other than the single crystal of silicon, for example, a silicon compound film such as a silicon oxide film or a silicon nitride film or the like, a metal coating film, a polycrystal silicon film, or other general thin film formed by steps of CVD (Chemical Vapor Deposition), sputtering, vapor deposition and the like. In that case a material testing device can be constituted by making the test piece spanned between a rigid supporting portion and a rotary lever comprising a single crystal of silicon.

A material testing apparatus according to the present invention is constituted by the material testing device, a load applying mechanism for applying a load on the rotary lever to thereby apply a uniaxial tensile force on the test piece, and a rotation detecting mechanism for detecting a rotation of the rotary lever.

A method of testing a material using the material testing device of the present invention comprises a step of applying a uniaxial tensile force on a test piece by applying a load on the rotary lever, a step of calculating a displacement of a point of loading at the rotary lever by detecting the rotation of the rotary lever, a step of calculating an amount of elongation of the test piece from the displacement of the point of loading at the rotary lever, a step of calculating a tensile force applied on the test piece by subtracting a deformation torque of the elastic supporting portion from the load applied on the rotary lever, and a step of calculating mechanical property values of a material of the test piece from the calculated amount of elongation of the test piece and the calculated tensile force.

Incidentally, it is apparent that when only a portion of the mechanical properties, for example, strain at breaking elongation, or only breaking stress is intended to be measured only portions of the steps may pertinently be selected.

According to the new system of the micro uniaxial tensile testing method by the material testing device, the material testing apparatus and the material testing method, the tensile test piece and the load applying mechanism are integrated to the same silicon wafer whereby the uniaxial tensile stress can be applied with no direct contact to the test piece. Also, the load applying mechanism includes a mechanism of magnifying the elongation deformation at one end of the test piece by which the elongation deformation can be detected by magnifying it. Accordingly, the mechanical property values of a very small material or a brittle material can be measured and evaluated easily and accurately by the present invention.

A detailed explanation will be given of the present invention in accordance with embodiments as follows. FIG. 1 is a perspective view showing an example of a material testing device 1 according to the present invention. The material testing device 1 is constituted by a test piece 2 the mechanical properties of which are to be measured, a flexing portion or rotary lever 3 connected to the test piece 2, a couple of torsion bars 4 operating as the elastic supporting portion of the rotary lever 3 and a main body portion or frame 5 functioning as the rigid supporting portion of the test piece 2 and the torsion bars 4 and forming the outside frame of the material testing device 1. A total of the material testing device 1 is integrally formed by, a single piece of material such as for example, a single crystal of silicon. In this embodiment, the rotary lever 3 comprises a cantilever portion having a first end 3a supported by the frame 5 and a second free end 3b for flexing in response to an external load applied directly thereto. The frame has a first pair of spaced-apart members 5a,5b and a second pair of spaced-apart members 5c,5d connected to the first pair of spaced-apart members to define an opening 5e therebetween. The member 5c of the frame 5 is connected to the test portion 2, and the torsion bars 4 are each connected to members 5a and 5b of the frame 5, respectively.

According to the material testing device 1, the mechanical properties of the test piece 2 are measured by applying a vertical load W at one end of the rotary lever 3 thereby causing a uniaxial tensile force in the test piece 2 in a direction of arrow marks A—A. The test piece 2 is integrally formed with the frame 5 and the rotary lever 3 and therefore, only the frame 5 is fixed and the mechanical properties of a test piece that is difficult to chuck or adhere to a tester can easily be measured since there is no need of direct contact on the test piece 2.

Figure 2:
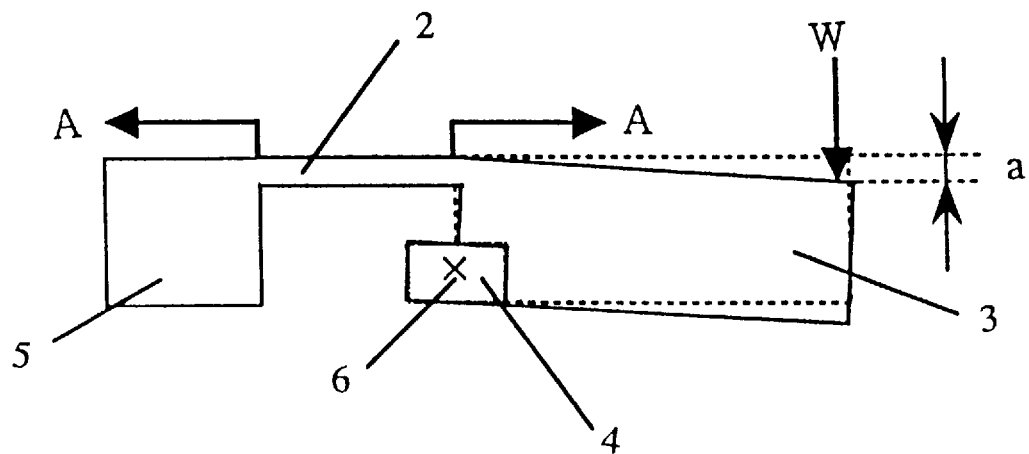
FIG. 2 is a sectional view showing the operation of the material testing device according to the present invention.

FIG. 2 is a sectional view showing a behavior of operating the uniaxial force on the test piece 2 by the vertical load W. When the vertical load W is applied at one end of the rotary lever 3, the rotary lever 3 flexes and is rotated around a geometrical center axis 6 of the torsion bars 4 by which the uniaxial tensile force in the direction of the arrow marks A—A is applied on the test piece 2. A moment by the applied vertical load W is statically in balance with a sum of moments by the reaction of the torsion bars 4 and the reaction (tensile force in the horizontal direction) of the test piece 2.

The tensile force applied on the test piece 2 can be calculated by evaluating the torque-rotational angle characteristic of the torsion bars 4 after the test and subtracting it therefrom. Meanwhile, the strain of the test piece 2 is calculated from a displacement "a" at a point of loading of the rotary lever 3.

Figure 3:
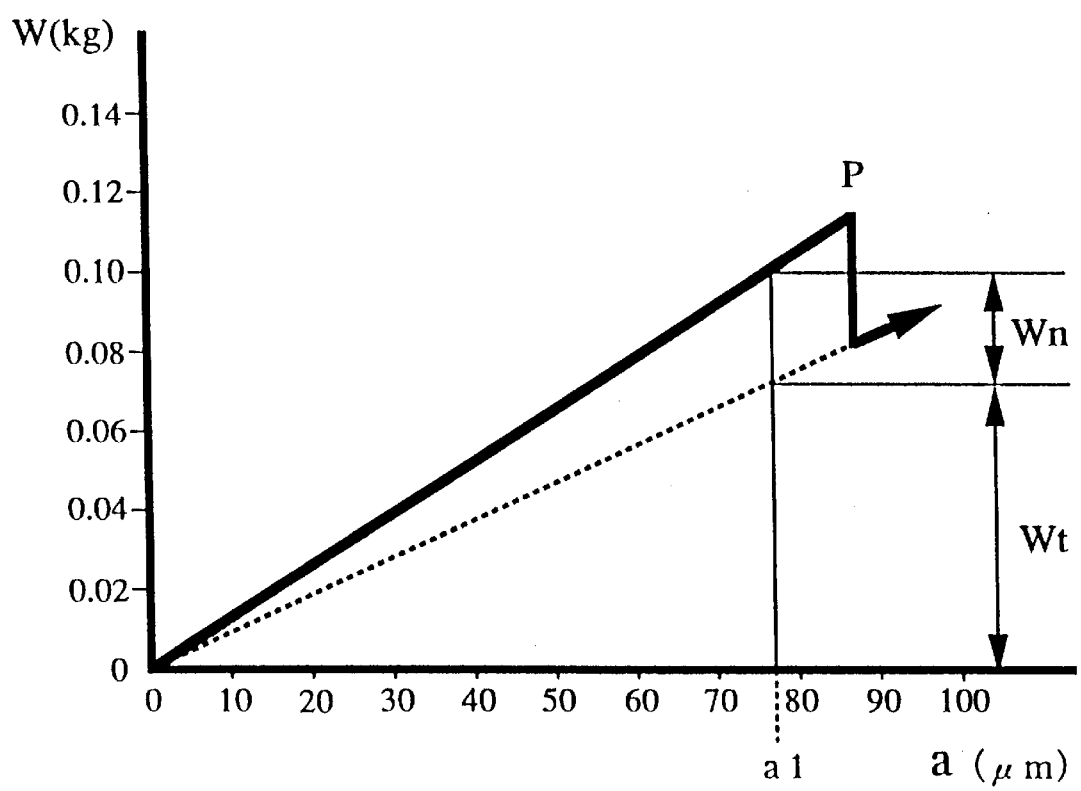
FIG. 3 is a diagram showing a relation between a displacement at a point of loading and a load according to the material testing device of the present invention.

The measurement result of the load W applied on the lever and the displacement "a" of the point of loading in the vertical direction in carrying out the tensile test with a single crystal of silicon as the test piece, is shown in FIG. 3. The load W is linearly increased with an increase in the displacement "a" pushing down the point of loading of the rotary lever as illustrated by a bold line in the figure. After the test piece is ruptured by tension at point P, the load is rapidly decreased to only a load required for the torsion torque of the torsion bars.

The deformation-load characteristic of the torsion bar per se which can be measured after the rupture of the test piece, is as illustrated by a broken line in the figure. When a load Wt required for the torsion torque of the torsion bars, is subtracted from the deformation-load characteristic of the test piece before rupture, a relation between a tensile load Wn actually applied on the test piece and the displacement "a" can be calculated.

For example, the stress "s" and the strain "e" caused in the test piece when the displacement of the end portion of the rotary lever is disposed at point a1 in FIG. 3 are calculated by the following calculation equations:

$$\text{Stress } s = (Wn \times R)/(A \times d)$$

$$\text{Strain } e = (a1 \times d)/(L \times R)$$

where, Wn: a load calculated by subtracting the load Wt required for the torsion torque of the torsion bars from the load W on the rotary lever, R: a distance in the horizontal direction (X direction in FIG. 4) between the center of rotation of the torsion bars and the point of loading of the rotary lever, A: a sectional area of the test piece, d: a distance in the vertical direction (Z direction in FIG. 4) between the center of rotation of the torsion bars and the axis of the test piece, a1: pushed-down displacement of the point of loading of the rotary lever, L: a length of the test piece As is known from the equation with respect to the value of the strain "e", the material testing device according to the present invention is provided with the structure where the ratio of values "R" to "d" is generally large and, therefore, a small strain can be measured by a comparatively large value of the displacement "a" of the rotary lever. That is, it signifies that the material testing device includes a mechanism of magnifying the elongation deformation of the test piece.

Next, an explanation will be given of conditions of causing the uniaxial tensile force in the tensile test piece in relation to the position and the shape of the torsion bars.

(1) Position of the torsion bars

Figure 4A:
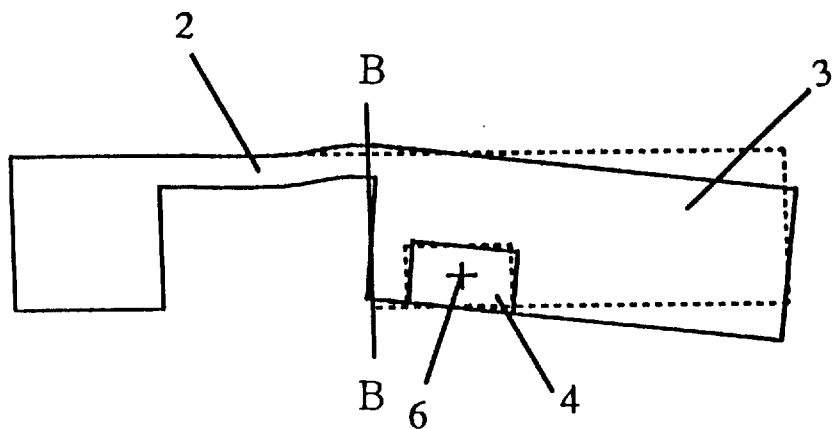
FIGS. 4(a)–(c) illustrate sectional views showing a position of torsion bars and a bending deformation of a test piece according to the material testing device of the present invention.

The geometrical center axis 6 of the torsion bars 4 is preferably positioned just below the one end of the tensile test piece as shown by FIG. 2. When the geometrical center axis 6 of the torsion bars 4 is not disposed just below the one end of the tensile test piece 2 as shown by FIG. 4(a), the one end of the test piece 2 is displaced in the up and down direction with the rotation of the rotary lever 3 and, accordingly, an inappropriate bending stress is caused in the test piece 2. Accordingly, the center axis 6 of the torsion bars 4 is set to position on a line B—B in FIG. 4(a).

(2) Dimensions of the section of the torsion bars

Figure 4B:
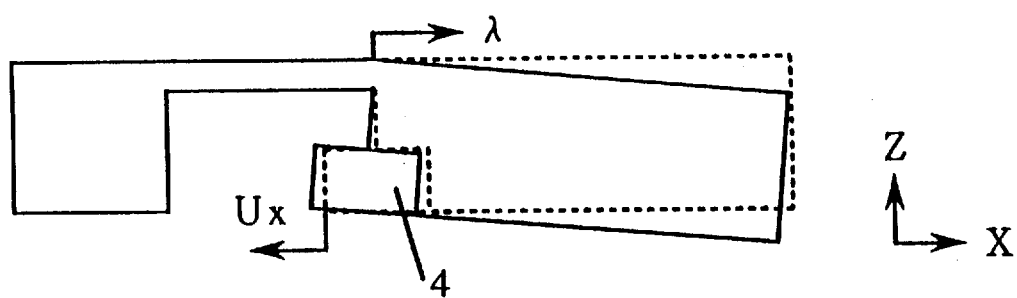
Figure 4C:
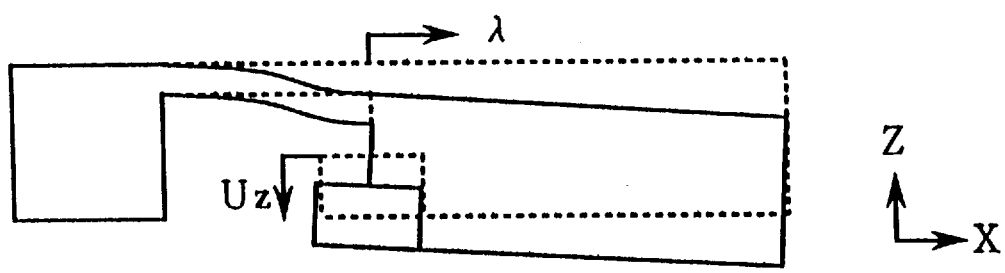
Figure 5:
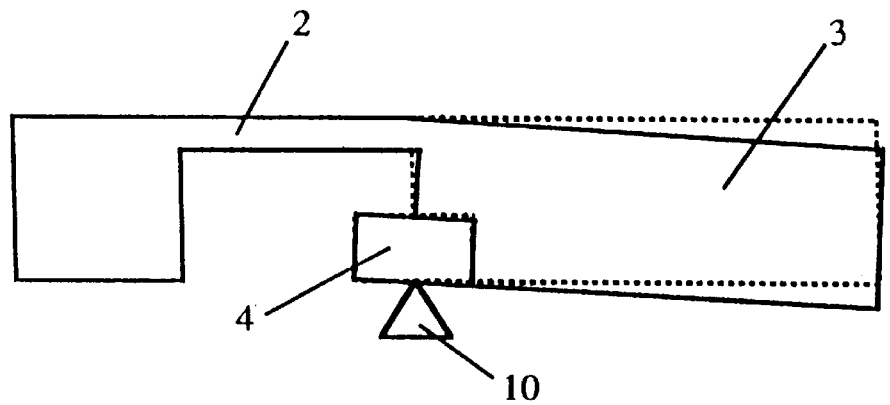
FIG. 5 is a sectional view showing an example of a method of supporting the torsion bars according to the material testing device of the present invention.

The torsional rigidity of the torsion bars 4 must be low and the bending rigidity thereof must be high. When the bending rigidity in the X direction in FIG. 4 is low, a displacement Ux in the X direction is caused in the torsion bars 4 as illustrated by FIG. 4(b) whereby a sufficiently accurate tensile displacement λ cannot be applied in the tensile test piece. Meanwhile, when the bending rigidity in the Z direction of FIG. 4 is low, a displacement Uz in the Z direction is caused in the torsion bars 4 as shown by FIG. 4(c) whereby a bending stress is superposed on the test piece and accordingly, the sufficient tensile displacement λ cannot be applied also in this case. However, the small magnitude of the bending rigidity in the Z direction becomes nonproblematic by supporting the portion right below the torsion bars 4 by a knife edge 10 as shown by FIG. 5. Therefore, according to such a supporting system, the sectional shape of the torsion bar 4 is preferable to have a flat section.

Figure 6A:
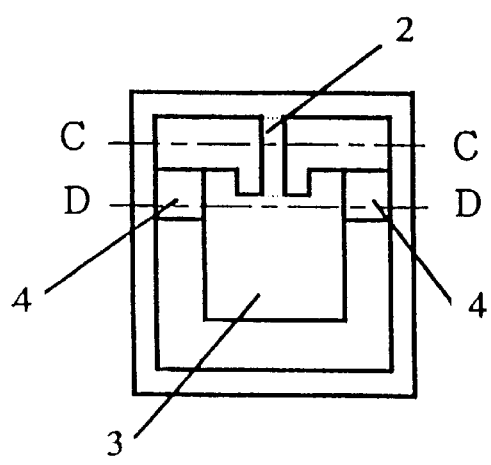
FIG. 6(a) is a view of a material testing device of the present invention in view from the top face.
Figure 6B:
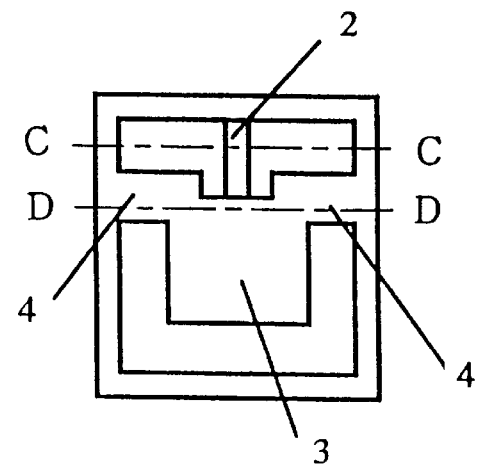
FIG. 6(b) is a view of a material testing device of the present invention in view from the bottom face.

Here, an example of various dimensions of a representative material testing device is described below. Outer frame: length 12 mm, width 12 mm, thickness 400 µm Test piece: thickness 5–20 µm, width 50–300 µm, length 1 mm Torsion bar: thickness 200–300 µm, width 400–1200 µm Rotary lever: width 3 mm, length 5 mm, thickness 400 µm The material testing device for the tensile test is manufactured by the micro machining technology of silicon finely and reproducibly. An explanation will be given of the method of manufacturing thereof as follows. Here, an explanation will be given of an example of a method of manufacturing a material testing device having a shape as illustrated by FIGS. 6(a) and 6(b) from a single crystal silicon wafer. FIG. 6(a) is a top view of the material testing device and FIG. 6(b) is a bottom view thereof.

Figure 7A:
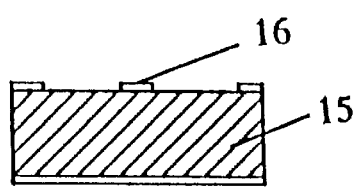
FIGS. 7 (a)–(n) illustrate views showing steps of machining the material testing device of the present invention.

The material testing device is manufactured by machining a single crystal silicon wafer by chemical anisotropic etching using an aqueous solution of KOH. FIGS. 7(a) through 7(n) show steps thereof where FIGS. 7(a) through 7(g) show steps in view of a section taken along a line C—C which is a portion including the test piece 2 in FIG. 6 and FIGS. 7(h) through (n) show steps in view of a section taken from a line D—D which is a portion including the torsion bars 4 in FIG. 6. As the material of the device a single crystal silicon wafer (face orientation: {100}, thickness: 400 µm) was used and a thermally-oxidized film of silicon (thickness: 0.6–2.2 µm) was used for the mask material in etching.

Figure 7H:
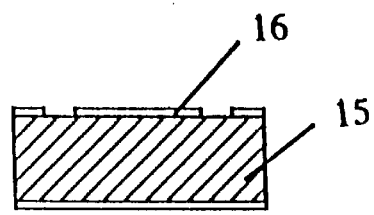
Figure 7B:
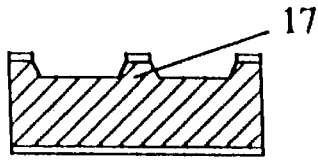
Figure 7I:
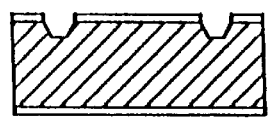
Figure 7C:
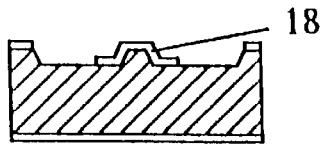
Figure 7J:
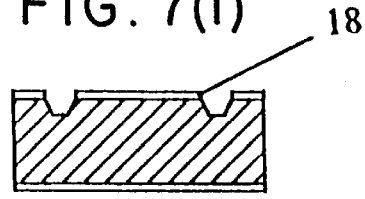
Figure 7D:
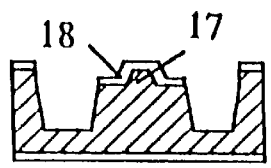
Figure 7K:
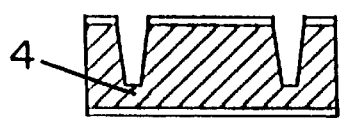
Figure 7E:
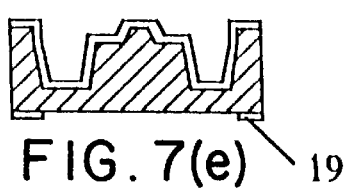
Figure 7L:
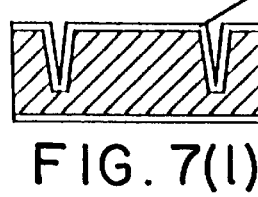
Figure 7F:
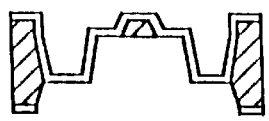
Figure 7M:
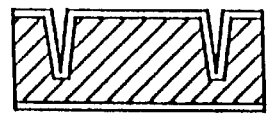
Figure 7G:
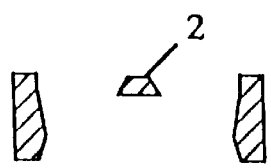
Figure 7N:
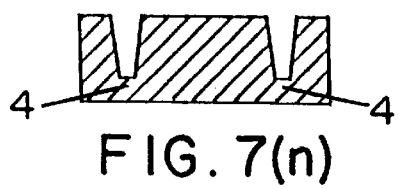

First, a thermally-oxidized film 16 is formed on the surface of the silicon wafer 15 in a first thermal oxidation step and the thermally-oxidized film is partially removed to form a predetermined shape as illustrated by FIGS. 7(a) and 7(h). In a first etching step of FIGS. 7(b) and 7(i), a profile 17 of the test piece is determined. Successively, in a second thermal oxidation step, a thermally-oxidized film 18 is formed again on the surface of silicon and the thermally-oxidized film is partially removed to form a predetermined shape as shown by FIGS. 7(c) and 7(j). In a second etching step of FIGS. 7(d) and 7(k), the etching is carried out until etched portions 14 are provided with the thickness of the torsion bars. In this procedure the profile 17 of the test piece is protected by an oxide film mask 18. In a third thermal oxidation step a thermally-oxidized film 19 is formed again on the surface of silicon and the thermally-oxidized film is partially removed to form a predetermined shape as illustrated by FIGS. 7(e) and 7(l). In a third etching step of FIGS. 7(f) and 7(m), an etching is carried out from the back side to form the profile of the torsion bars 4. The amount of etching here determines the thickness of the test piece 2. FIGS. 7(g) and 7(n) illustrate respective sections of the completed material testing device where the test piece 2 and the torsion bars 4 can be formed reproducibly in the predetermined profiles and thicknesses, respectively.

If the material for the tensile test is intended to be a silicon oxide film or a silicon nitride film, these films are formed on the top face of a portion of the device corresponding to the test piece and the single crystal of silicon beneath the test piece is completely removed in the third etching whereby only these films are spanned between the rotary lever and the support frame as the test piece. The reason is that these films have a resistance against the etching by KOH.

If other materials having the resistance against the etching by KOH, for example, a film formed by plating nickel, are the test pieces, after these films on the top face of a portion of the device corresponding to the test piece are formed by a step of sputtering, vapor deposition or the like prior to the third etching, the single crystal of silicon of the portion corresponding to the test piece is completely removed in the third etching whereby the material testing device can similarly be formed.

Further, if the tested material is a material having no resistance against the etching by KOH, for example, a polycrystal silicon film, after protecting the film by a third material having the etching resistance from above and from below, the etching of the single crystal of silicon is carried out and finally the third material is selectively removed. As the third material, a silicon oxide film, a silicon nitride film, a nickel film and the like are suitable.

Figure 8:
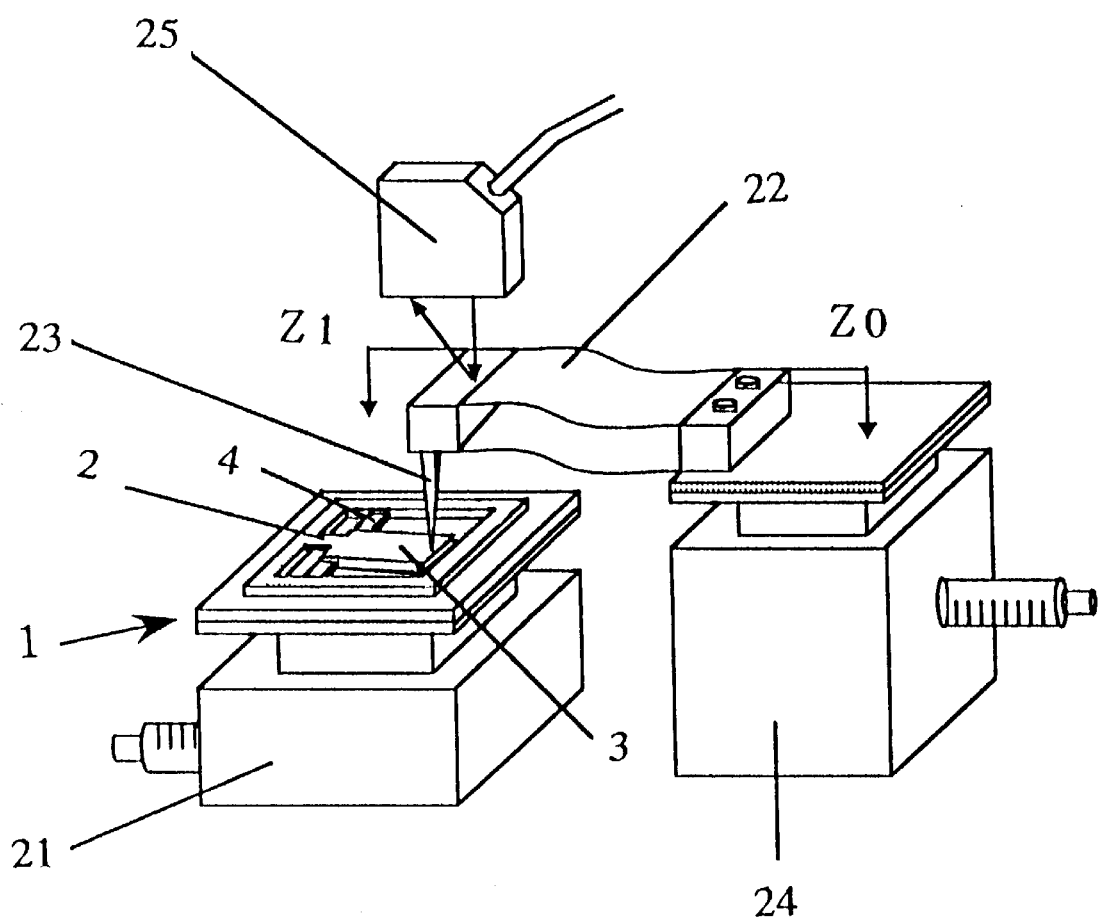
FIG. 8 is a perspective view showing an embodiment of a material testing apparatus of the present invention.
Figure 9:
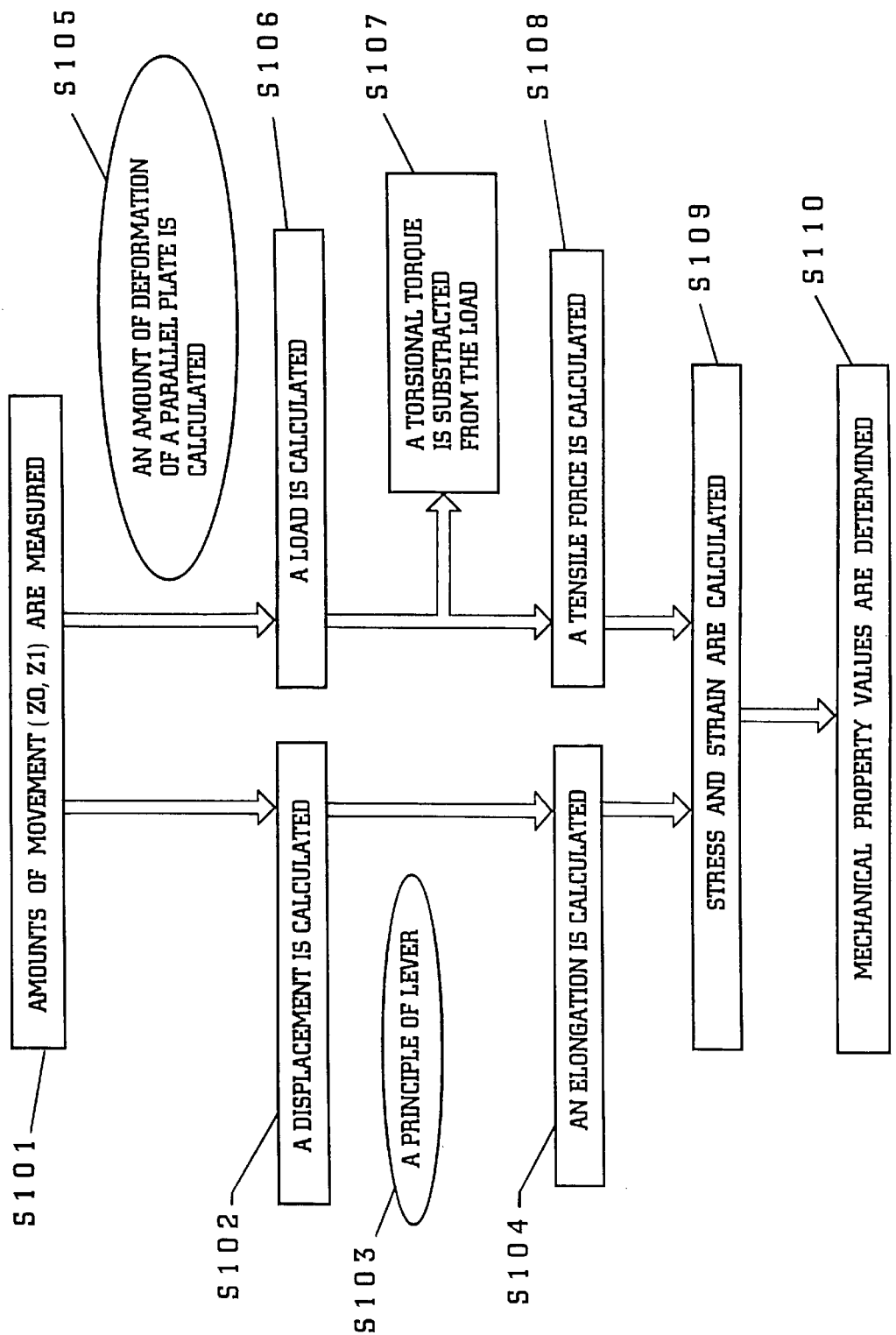
FIG. 9 is a step diagram showing an embodiment of a material testing method of the present invention.

FIG. 8 and FIG. 9 respectively show a material testing apparatus and a material testing method for the above-described tensile-test. In FIG. 8 a material testing device 1 is mounted on a X-Y-Z-θ stage 21. A needle 23 attached to a front end of a parallel plate spring 22 applies a vertical load on the rotary lever 3 of the material testing device 1. The root of the parallel plate spring 22 is fixed to a Z stage 24 and by pertinently moving upwardly and downwardly the Z stage 24 a load corresponding to an amount of displacement of the parallel plate spring 22 can be applied on the rotary lever 3. The stress and strain caused in the test piece 2 can be calculated by detecting the load applied on the needle 23 and the displacement of the point of loading in the vertical direction.

The displacement of the point of loading can directly be measured by a laser type length measuring machine 25 while the load is calculated from the amount of displacement of the parallel plate spring 22. The amount of displacement of the parallel plate spring 22 is calculated by respectively measuring amounts of moving in the up and down direction Z0 and Z1 of the root and the front end thereof and calculating a difference therebetween.

Although the torsional rigidity of the torsion bars 4 can be calculated from the shape of the torsion bars 4, it can be calculated by evaluating the torque-rotational angle characteristic of the torsion bars 4 by applying a load on the rotary lever 3 by the needle 23 at the front end of the parallel plate spring 22 again after the test piece 2 has been ruptured by tension.

Incidentally, with regard to the detection of the elongation of the test piece, other than the above-described method where the amount of pushing down the lever is detected, the elongation displacement of the test piece can also be calculated by measuring the rotational angle of the lever under the principle of "optical lever" where the laser beam is irradiated on the surface of the rotary lever and using the value.

In any case, the mechanical property values can accurately be measured generally with respect to a brittle material and also a thin film material having a small elongation strain by using the material testing device and the material testing apparatus of the present invention.

FIG. 9 is a flowchart showing steps of calculating the mechanical property values of a material by the above-described material testing apparatus. In step 101 (hereinafter, S101) the amounts of movement in the up and down direction Z0 and Z1 of the root and the front end of the parallel plate spring 22 are respectively measured. In step S102, the displacement of the point of loading of the rotary lever 3 is calculated from the measured value Z1. In step S103, the calculation according to the principle of lever is carried out from the displacement of the point of loading of the rotary lever 3 and in step S104, the elongation of the test piece 2 is calculated. In step S105 the amount of deformation of the parallel plate spring 22 is calculated from the measured values Z0 and Z1 and in step S106, the load applied on the rotary lever 3 by the needle 23 is calculated. In S107, the component derived from the torsional torque by the torsion bars 4 is subtracted from the load applied on the rotary lever 3 and in step S108, the tensile force applied on the test piece 2 is calculated. In step S109, the stress and strain caused in the test piece 2 are calculated from the elongation of the test piece 2 calculated in step S104 and the tensile force applied on the test piece 2 calculated in step S108, and in step S110 the mechanical property values of the test material are determined from the calculation results.

The procedure of the material testing method according to the present invention has been explained as described above. The step S101 of calculating the measured values and the step S105 of calculating the amount of deformation may pertinently be changed if the means for applying the load is changed, in accordance with the changed means.

As described above, three advantages are enumerated with respect to the new tensile test according to the present invention.

(1) There is no need of manipulating a very small test piece that is easy to destruct and formed on a wafer.

(2) The displacement of the one end of the very small test piece is detected by magnifying it as the displacement at the point of loading (end of lever) under the principle of lever.

(3) With respect to the material of the test piece, other than the single crystal of silicon, various thin film materials formed on the surface of a wafer can be used.

Further, by using such a device, the test can be carried out not only with respect to the mechanical property values, particularly the yield stress, the tensile strength, the elastic modulus and the like of various thin film materials formed on the surface of a silicon wafer but with respect to fatigue by applying a repeated load thereon. Further, if the film is prepared as a test piece, the film is subjected to processes of ion implantation, heat treatment or the like and the rotation of the rotary lever thereby is measured, elongation or contraction of the film can also be detected.

Meanwhile, the device can also be used as a means for observing a change in a film while causing a constant stress in a thin film material, such as observing a change in the structure of the film material while causing a constant tensile stress in the film. At this occasion, as the stress applying mechanism and the observing means, for example, the ultrasonic microscope system and the Raman spectroscopic analysis system and the like may be used in combinations.

As described above the following effects are provided by the present invention.

(1) There is no need of manipulating a very small test piece that is easy to destruct and formed on a wafer.

(2) The displacement of the one end of the very small test piece is detected by magnifying it as the displacement of the point of loading (end of lever) under the principle of lever.

(3) Other than the single crystal of silicon, various thin film materials can be used as the material of the test piece.

(4) Other than the tensile test the fatigue test of a thin film can be carried out.

(5) A change in a thin film can be observed in a state where a constant tensile stress is caused in the thin film material.

What is claimed is:

1. A material testing device comprising:
   a test piece;
   a rotary lever for applying a predetermined stress on the test piece;
   at least one elastic support portion for elastically supporting the rotary lever; and
   a rigid support portion for rigidly supporting the test piece and the elastic support portion;
   wherein the test piece, the rotary lever, the elastic support portion and the rigid support portion are constituted integrally by a single crystal of silicon.

2. A material testing device according to claim 1; wherein the test piece is comprised of a thin film of material extending between the rigid support portion and the rotary lever.

3. A material testing device according to claim 1; wherein the rotary lever is not supported directly by the rigid support portion.

4. A material testing device according to claim 1; wherein the rotary lever comprises a cantilever portion having a first end supported by the rigid support portion and a second free end for flexing in response to an external load applied directly thereto to apply a predetermined stress on the test piece.

5. A material testing device comprising: a single crystal of silicon having a main body portion, a flexing portion connected to the main body portion for flexing in response to an external load applied thereto, and a test portion connected to the main body portion for receiving a predetermined stress in response to the external load applied to the flexing portion.

6. A material testing device according to claim 5; further comprising a plurality of connecting portions for connecting the flexing portion to the main body portion.

7. A material testing device according to claim 7; wherein the connecting portions comprise elastic support portions for elastically supporting the flexing portion to the main body portion.

8. A material testing device according to claim 5; wherein the flexing portion comprises a cantilever portion having a first end connected to the main body portion and a second free end for receiving the external load directly thereto.

9. A material testing device according to claim 8; wherein the test portion is connected between the main body portion and the first end of the cantilever portion.

10. A material testing device according to claim 5; wherein the single crystal of silicon has a pair of connecting portions for connecting the flexing portion to the main body portion; and wherein the main body portion has a first pair of spaced-apart members and a second pair of spaced apart-members connected to the first pair of spaced-apart members to define an opening therebetween, one of the members of the first pair of spaced-apart members being connected to the test portion, and the members of the second pair of spaced-apart members being connected to a respective one of the connecting portions.

11. A material testing device according to claim 5; wherein the testing portion comprises a thin film extending between the main body portion and the flexing portion.

12. A material testing apparatus comprising:
 a material testing device having a test piece, a rotary lever for applying a predetermined stress on the test piece, at least one elastic support portion for elastically supporting the rotary lever, and a rigid support portion for rigidly supporting the test piece and the elastic support portion; the test piece, the rotary lever, the elastic support portion and the rigid support portion being constituted integrally by a single crystal of silicon;
 a load applying mechanism for applying a uniaxial tensile force on the test piece by applying a load on the rotary lever; and
 a rotation detecting mechanism for detecting a rotation of the rotary lever.

13. A method of testing a material, comprising the steps of:
 providing a material testing device comprising a test piece, a rotary lever for applying a predetermined stress on the test piece, at least one elastic support portion for elastically supporting the rotary lever, and a rigid support portion for rigidly supporting the test piece and the elastic support member; the test piece, the rotary lever, the elastic support portion and the rigid support portion being constituted integrally by a single crystal of silicon;
 applying a uniaxial tensile force on the test piece by applying a load on the rotary lever;
 calculating a displacement at a point of the rotary lever where the load is applied by detecting a rotation of the rotary lever;
 calculating an amount of elongation of the test piece from the displacement at the point of the rotary lever where the load is applied;
 calculating a tensile force applied on the test piece by subtracting a deformation torque of the elastic support portion from the load applied on the rotary lever; and
 calculating mechanical property values of a material of the test piece from the calculated amount of elongation of the test piece and the calculated tensile force.

14. A material testing apparatus comprising: a material testing device comprised of a single crystal of silicon having a main body portion, a flexing portion connected to the main body portion for flexing in response to an external load applied directly thereto, and a test portion connected to the main body portion for receiving a predetermined stress in response to the external load applied to the flexing portion; a load applying mechanism for applying the external load directly to the flexing portion; and a detecting mechanism for detecting flexion of the flexing portion upon application of the external load thereto by the load applying mechanism.

15. A material testing apparatus according to claim 14; further comprising a plurality of connecting portions for connecting the flexing portion to the main body portion.

16. A material testing device according to claim 15; wherein the connecting portions comprise elastic support portions for elastically supporting the flexing portion to the main body portion.

17. A method of testing a material, comprising the steps of: providing a material testing device comprised of a single crystal of silicon having a main body portion, a flexing portion connected to the main body portion for flexing in response to an external load applied directly thereto, at least one elastic connecting portion for elastically connecting the flexing portion to the main body portion, and a test portion connected to the main body portion for receiving a predetermined stress in response to the external load applied to the flexing portion; applying an external load directly at a point on the flexing portion to flex the flexing portion to apply a predetermined stress to the test portion; calculating a displacement of the flexing portion at the point thereof where the external load has been applied by detecting the flexion of the flexing portion; and calculating an amount of elongation of the test portion on the basis of the calculated displacement of the flexing portion.

18. A method according to claim 17; further comprising calculating a tensile force applied on the test portion by subtracting a deformation torque of the elastic connecting portion, resulting from the application of the external load on the flexing portion, from the external load applied on the flexing portion.

* * * * *